(12) United States Patent (10) Patent No.: US 9,084,690 B2
Pedersen et al. (45) Date of Patent: Jul. 21, 2015

(54) AID DEVICE INCLUDING A TOOL AND AN ATTACHING OF THE TOOL

(75) Inventors: Hans Joergen Pedersen, Harrislee (DE); Jesper Allan Hansen, Broager (DK)

(73) Assignee: Invencon ApS, Nordborg (DK)

( * ) Notice: Subject to any disclaimer, the term of this patent is extended or adjusted under 35 U.S.C. 154(b) by 0 days.

(21) Appl. No.: 13/520,608

(22) PCT Filed: May 6, 2011

(86) PCT No.: PCT/DK2011/000044
§ 371 (c)(1),
(2), (4) Date: Sep. 26, 2012

(87) PCT Pub. No.: WO2011/137904
PCT Pub. Date: Nov. 10, 2011

(65) Prior Publication Data
US 2013/0035771 A1 Feb. 7, 2013

(30) Foreign Application Priority Data
May 6, 2010 (DK) .................................. 2010 00398

(51) Int. Cl.
*A61F 2/68* (2006.01)
*B65G 7/12* (2006.01)
*B66F 19/00* (2006.01)
*A61F 2/54* (2006.01)

(52) U.S. Cl.
CPC .... *A61F 2/68* (2013.01); *B65G 7/12* (2013.01)

(58) Field of Classification Search
USPC ........ 623/65; 294/25, 213; 81/90.3, 90.9, 127
See application file for complete search history.

(56) References Cited

U.S. PATENT DOCUMENTS

| 1,388,618 | A | * | 8/1921 | Stein et al. ........................... 2/21 |
| 1,990,553 | A | * | 2/1935 | Hirsch et al. ........................ 2/20 |
| 2,858,947 | A | * | 11/1958 | Chapman, Jr. .................... 414/5 |
| 3,735,426 | A | * | 5/1973 | Horvath ......................... 623/65 |
| 3,781,052 | A | * | 12/1973 | Millington ..................... 294/25 |

(Continued)

FOREIGN PATENT DOCUMENTS

| CA | 2148577 C | 1/2007 |
| WO | 2008/036746 A2 | 3/2008 |

OTHER PUBLICATIONS

International Search Report for PCT Serial No. PCT/DK2011/000044 dated Aug. 2, 2011.

(Continued)

*Primary Examiner* — Jacqueline Woznicki
(74) *Attorney, Agent, or Firm* — McCormick, Paulding & Huber LLP

(57) ABSTRACT

This invention relates to aid devices for assisting people inhibited in their movement of especially the hands and/or wrists, such as people who are physically impaired due to arthritis, injury, or other physiological problems giving reduced strength. This is solved by introducing an aid tool comprising at least two grippers and means to attach each gripper to a finger of a person, where the grippers are adapted to follow the individual finger in a movement in the direction of closing and loosen of a grip, and where an activation of the aid tool includes locking the grippers unidirectionally in the present position. The invention further introduces mounting means for attaching the aid tool to a body part, and where the mounting means comprises coupling means for detaching and attaching this and other tools according to the need.

8 Claims, 13 Drawing Sheets

(56) References Cited

U.S. PATENT DOCUMENTS

| | | | |
|---|---|---|---|
| 3,862,507 A * | 1/1975 | Martyn | 43/4 |
| 3,967,321 A * | 7/1976 | Ryan et al. | 623/24 |
| 4,035,865 A * | 7/1977 | McRae et al. | 16/426 |
| 4,149,532 A | 4/1979 | Terry et al. | |
| 4,167,044 A | 9/1979 | Girard | |
| 4,180,870 A | 1/1980 | Radulovic et al. | |
| 4,252,360 A * | 2/1981 | Gallaher, Jr. | 414/732 |
| 4,523,781 A * | 6/1985 | Brody | 294/25 |
| 4,846,518 A * | 7/1989 | Hamel | 294/99.1 |
| 4,884,581 A * | 12/1989 | Rescigno | 128/869 |
| 5,002,561 A * | 3/1991 | Fisher | 606/210 |
| 5,413,611 A * | 5/1995 | Haslam et al. | 623/25 |
| 5,770,297 A * | 6/1998 | Grubich | 428/99 |
| 5,800,561 A | 9/1998 | Rodriguez | |
| 5,853,210 A * | 12/1998 | Robinson | 294/25 |
| 6,059,694 A * | 5/2000 | Villepigue | 482/47 |
| 6,739,220 B1 | 5/2004 | Johnson et al. | |
| 6,866,314 B2 * | 3/2005 | Cho | 294/99.2 |
| 6,879,880 B2 * | 4/2005 | Nowlin et al. | 700/260 |
| 2003/0218344 A1 * | 11/2003 | Garrett | 294/25 |
| 2004/0135387 A1 * | 7/2004 | Keith et al. | 294/19.1 |
| 2005/0250994 A1 | 11/2005 | Krullaards | |
| 2008/0232932 A1 * | 9/2008 | Jinno | 414/4 |
| 2010/0092267 A1 * | 4/2010 | Najdovski et al. | 414/7 |
| 2011/0041349 A1 * | 2/2011 | Zimmermann et al. | 30/322 |
| 2012/0059291 A1 | 3/2012 | Nguyen | |
| 2013/0277993 A1 * | 10/2013 | Zimmermann et al. | 294/25 |

OTHER PUBLICATIONS

Article entitled "An Orthotic Hand-Assistive Exoskeleton for Actuated Pinch and Grasp" by M. F. Rotella, et al.; The College of New Jersey; presented at Bioengineering Conference 2009; I EEE 35th Annual Northeast I EEE, Apr. 3, 2009; 2 pages.

* cited by examiner

AID DEVICE INCLUDING A TOOL AND AN ATTACHING OF THE TOOL

CROSS REFERENCE TO RELATED APPLICATIONS

This application is entitled to the benefit of and incorporates by reference essential subject matter disclosed in International Patent Application No. PCT/DK2011/000044 filed on May 6, 2011 and Danish Patent Application No. PA 2010 00398 filed May 6, 2010.

TECHNICAL FIELD

This invention relates to aid devices for assisting people inhibited in their movement of especially the hands and/or wrists, such as people who are physically impaired due to arthritis, injury, or other physiological problems giving reduced strength. This is solved by introducing an aid tool with at least two grippers and means to attach each gripper to a finger of a person, where the grippers are adapted to follow the finger(s) in at least the directions to grab and release an object. When the aid tool has been moved to grab an object by a person, an activation of the aid tool ensures a unidirectional locking of the grippers, meaning they are locked in their movement in the releasing direction. The invention further introduces mounting means for attaching the aid tool to a body part, where the mounting means comprises coupling means for detaching and attaching this and other tools according to the need.

BACKGROUND OF THE INVENTION

This invention relates to aid devices for assisting people inhibited in their movement of especially the hands and/or wrists, such as people who are physically impaired due to arthritis, injury, or other physiological problems giving reduced strength.

A substantial number of people suffer from deformations, chronic pain, and other impairments of the hands and wrists, due to injuries or various diseases such as rheumatoid or other forms of arthritis. Such impairments often render it difficult or impossible for the affected people to hold and effectively to use and handle tools, for example such as a pen, pencil, or other writing instrument, scissors, toothbrushes, kitchen utensils (such as knives, forks, stirrers, spatulas, etc.), and the like.

Many such people are able move their arm, and even fingers, but need strength to grip devices and hold them firmly.

The aim of the present invention therefore is to introduce a device, either single- or multi-purpose aid device, which can assist or enable people with physically impaired hands and/or wrists to hold and use various hand-held tools and devices (such as toothbrushes, keys, scissors, tongs, and kitchen utensils) with greater ease, where the invention especially introduces a tool to assist gripping objects firmly, this being especially suited for users able to move their arms, hands and fingers, only having no strength to take a firm grip on objects. Especially it is an aim of the present invention to introduce a device with grippers to be placed between the user's fingers and an object to be held, so that the holding force exerted by the aid tool does not affect the fingers but only increases the pressure between the grippers of the aid tool and the object.

SUMMARY

This is solved by introducing an aid tool comprising at least two grippers and means to attach each gripper to a finger of a person, where the grippers are adapted to follow the individual finger in at least the directions to grab and release an object. When the aid tool has been moved to grab an object by a person, an activation of the aid tool ensures a unidirectional locking of the grippers, meaning they are locked in their movement in the releasing direction In this manner the users may themselves move the hand and thereby the aid tool to the object and grab it. The grippers follow the fingers in at least the directions to grab and release an object and a hold force, in the following a hold, on the object is subsequently established to ensure a firm grip even though the user has no significant strength. This hold is formed by the aid tool being adapted to tighten the grip on the object a little more than the strength of the grip at the time of activation.

In one embodiment this hold is achieved by letting at least some of the grippers comprise an inflatable section, or at least expandable contact section, being inflated or expanded when the aid tool is activated. These sections then form the contact to the object. Inflatable or expandable in the present context means they when activated will form protrusions above the surface of the grippers. The inflatable or expandable contact sections preferably have contact surfaces to the object with high friction.

In an alternative embodiment this hold is achieved by letting the grippers move in the grapping direction to form a slightly more tight grab than when the aid tool was activated, and where the grippers comprises elastically deformable contact sections to be in contact with the object. The elastically deformable contact sections are such that they will conform a little to the surface of the object, such both giving a more 'soft' contact to the object, thus helping to prevent it from being damaged, and in addition giving an even further tightened grab of the object. Again the surface of these contact surfaces may be such that they have a high friction.

The aid tool in one embodiment is activated by activating at least one activation switch at a predetermined force. In one embodiment the switch is positioned on a gripper between the gripper and a finger, and is adapted to be activated when the finger press on the activation switch at the predetermined force. The user therefore needs no significant strength in the fingers to use the device, only slightly to push a switch.

In an alternative embodiment the activation switch is positioned such that it is to be activated by the other hand of the person.

To inflate the inflatable sections the aid tool further comprises means to fill a fluid media into the inner of the inflatable sections when the aid tool is activated. The aid tool in this configuration therefore comprises the needed means to fill a fluid media into the inflatable sections, such as for example a compressor, fluid communications, valves, vents and/or flow restrictors.

To secure the aid tool in a quick and easy exchangeable manner to a body part, the present invention further introduces mounting means adapted to be attached to a body part first coupling means comprising a biased catch having a first position and a second position holding mechanism adapted to hold the catch in the second position, releasing means adapted to release the catch from the holding mechanism, wherein the aid tool comprises second coupling means and where either the first coupling means or the second coupling means comprises a driving mechanism adapted to move the biased catch from a first to a second position.

The driving mechanism preferable is a pneumatic, hydraulic, piezo, electro-active, electrostrictive, electrical and/or magnetic actuator.

In more general, to ensure a quick attaching and detaching of the tool to and from the aid device, in one preferred embodiment the coupling of the first and second coupling means are based on a biased clutch, where different types of biased clutches as known in the art may be introduced such as spring clutch, a diaphragm spring, by pneumatics, strings, hydraulics, piezo motors, electrical and/or a magnetic spring clutch.

The aid tool may comprise energy storing means especially to be used in connection with the biased clutch or other energy consuming parts of the aid device.

The energy storing means may in one embodiment be recharged during handling of the tool, or during the attachment of the first and second coupling means.

In a further embodiment, the aid device may comprise electrical parts, such as a magnetic spring clutch, and may therefore comprise energy storing means for storing electrical energy, such as batteries.

In one embodiment the aid device is to be attached and detached to and from the body part in a base station, where the base station may be positioned at the home of the person, or at a place where it is operated by specialists.

DETAILED DESCRIPTION

Figure 1:
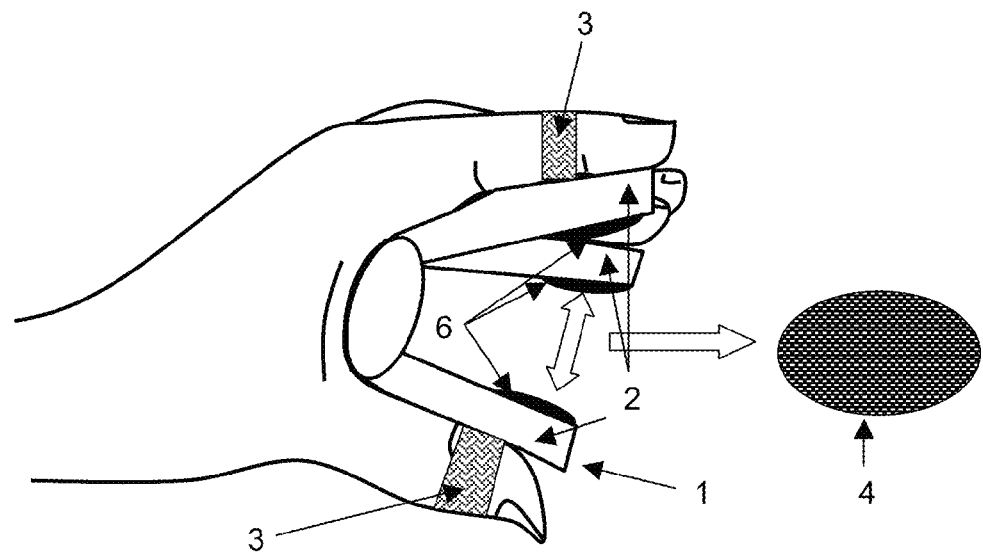
FIG. 1 is a simple illustration of the aid tool of the present invention.

FIG. 1 shows schematically the concept of an aid tool (1) according to the present invention, where the aid tool (1) comprises at least two grippers (2), in the illustration three, connected to some or all of the fingers such as by straps (3). In the preferred embodiment one of the grippers (2) is secured to the thumb.

The grippers (2) are able to move with the fingers at in at least the directions to grab and release an object (4) where the grippers are placed between the object and the fingers, thus avoiding pain to the fingers, when the aid tool (1) exercises its additional force, the hold.

The user of the aid tool (1) is preferably able to move the hand in connection with the object (4) and to move the fingers and thus the grippers (2).

Figure 2:
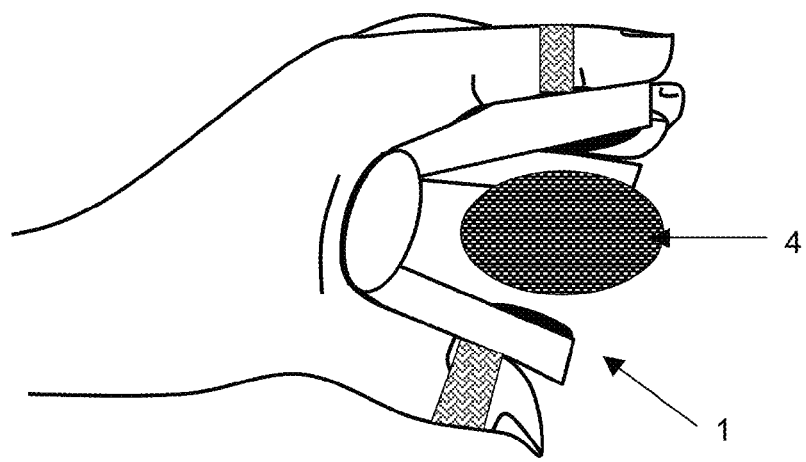
FIG. 2 shows the aid tool as it is in position to grip an object.

When the aid tool (1) is placed in connection with an object (4), FIG. 2, the user grabs on the object with the grippers (2), not the fingers, touching the object.

Figure 3:
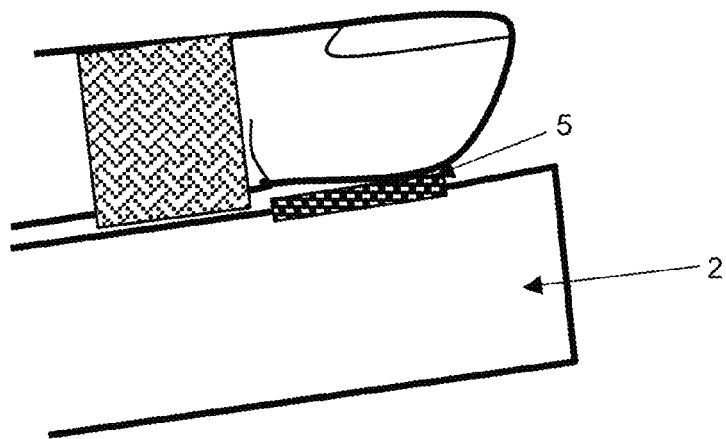
FIG. 3 is an illustration of a positioning of a switch to activate the aid tool of the present invention.

In the illustrated embodiment, at least one of the grippers (2) has an activation switch (5), see FIG. 3, positioned such that when the finger press the activation switch (5) with a pre-defined force, a gripper interlocking mechanism is activated (not illustrated) to lock preferably all the grippers (2) in their present position in an unidirectional manner meaning they are locked in their movement in the releasing direction but may be free to move in the grapping direction.

The aid tool (1) is further adapted to form a hold on an object (4), this hold being formed by tightening the grip on the object (4) a little more than the strength of the grip at the time of activation.

In one embodiment this hold is established in that at least some of the grippers (2) comprise a contact section (6) to the object (4) being an inflatable or expandable contact section adapted to form protrusions above the surface of the gripper when the aid tool (1) is activated, these protrusions forming at least part of the contact surface to the object (4).

Figure 4:
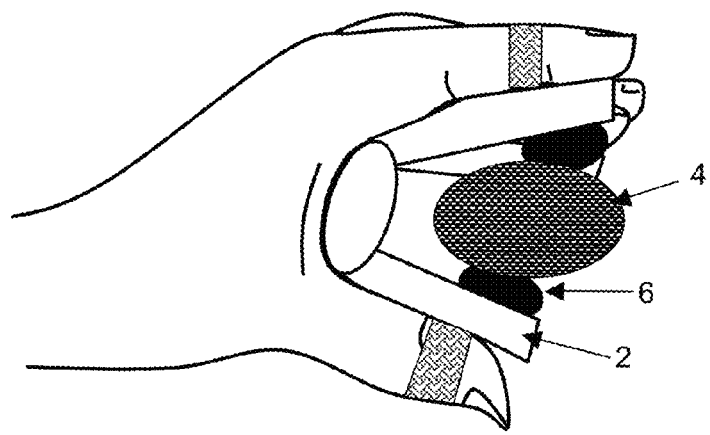
FIG. 4 is an illustration of inflated or expanded sections being in contact with an object.

When the aid tool (1) is activated by pressing the activation switches (5), the inflatable or expandable contact sections (6) inflate, much as a balloon, or expands (see FIG. 4), to a predetermined pressure or expansion level and reach out of the grippers (2) until they get into the desired degree of contact with the object (4). A combination of the unidirectional locked grippers (2), the inflatable or expandable contact sections (6) squeezing onto the object (4) and their high friction surfaces ensures a firm grip onto the object.

In an alternative or additional embodiment, the hold is established in a manner where the grippers (2) after activation move in the grapping direction to form a slightly tighter grab than at the time of activation. The grippers (2) may then comprise contact sections (6) being elastically deformable contact sections (6), such that they will conform a little to the surface of the object (4) giving a more 'soft' contact to the object, thus helping to prevent it from being damaged, and in addition giving an even further tightened grab of the object. Again the surface of these contact surfaces may be such that they have a high friction.

In one embodiment at least a significant part of the contact surface of the grippers (2) to the object (4) is made of or at least comprises a high friction material of any kind as known in the art.

The grippers (2) may automatically sense when they touch the object (4), for example due to the increased resistance to the drivers of the grippers (2). The system then optionally is deactivated and the grip released when the user deactivates the activation switches (5).

Alternatively the grippers (2) stop e.g. when the fingers release the activation switches (5), and then hold this position until the activation switch (5) is activated a next time.

The inflatable or expandable contact sections (6) optionally inflate or expand either as the grippers (2) are activated by pressing the activation switch (5), when they are set to hold the position or when they are activated a second time.

When the user wants to let the object free, the push of the fingers on the switch(es) is removed, thus removing the lock of the grippers (2) and deflating the inflatable or expandable contact sections (6). Alternatively one of the switch(es) (5) are dedicated to turn off the activation energy in order to bring the inflatable or expandable contact sections back into their original positions This only leaves the user to be able to move the arm and open and close the fingers, the activation switches (5) may only need a slight touch to be activated, where this may be an adjustable parameter of the aid tool (1), the activation force of the switch(es) (5) especially being adjusted according to the need of the individual user.

The same activation/deactivation of would also apply to the alternative or additional embodiment where the grab is tightened by a slightly further movement of the grippers (2) in the gripping direction.

The media inflating the inflatable sections (6) may be fluid like a gas like air or a liquid like water or oil. The device expanding the expandable contact sections may be a linear activator driven by electrical, piezoelectric, pneumatic or hydraulic means, or a form of an expandable polymer such as an electrostatically driven polymer actuation material The aid tool (1) would comprise the devices needed to perform the action of inflation or expansion and deflation or relaxation as well known in the art, such as a compressor, a fluid reservoir containing the fluid to inflate the sections (6), fluid communication means to connect e.g. the reservoir and the inflatable sections (6), valves, vents, flow restrictors etc. In one embodiment the media is air sucked to the inflatable sections (6) from the externals.

The grippers (2) may being operated by drivers, such as for example electrical, electrostatic, magnetic, pneumatic, hydraulic, mechanical or string means, such as by for example actuators of any kind as known in the art. These drivers may be controlled by pressing the activation switches (5) at the fingers at a predetermined force.

The expansion and relaxation of the inflatable or expandable contact sections (6) may be operated by pneumatics, strings, hydraulics, piezo motors, electrical and/or magnetic methods.

The inflatable or expandable contact sections (6) may be introduced as balloon-shaped or bladder like elements enclosed within deepenings in the grippers (2) and having at least part of the surface comprising a high friction material, the part of the surface to get in contact with objects (4). When the aid tool (1) is activated, to inflate or expand the sections (6) the internals of the balloon-shaped or bladder like elements then are filled with a media under predetermined pressures. Alternatively to the balloon-shape the deepenings may just have a cover of a substantially flexible material and with an external surface of a high friction material. When a media of a predetermined pressure is filled into the deepening the covers then bulges out from the surface of the grippers (2) to get in contact with the object (4).

In one advanced version the aid tool (1) further comprises means to sense the pressure of the inflatable or expandable contact sections (6) on the object (4), where this may be in connection with the needed pressure to squeeze media to the internals of the inflatable sections (6). When part of the surfaces of the inflatable sections gets in contact with the object (4) these parts are prevented from further extension/inflation, and thus adds to the pressure needed to squeeze further media into their internals. Thus by defining a maximum of this pressure, it is possible to regulate the pressure of the grippers (2) and inflatable sections (6) on the object (4).

Thus the inflatable sections (6) may optionally be filled at an adjustable predetermined pressure being adjusted according to the need of the individual user and/or be adjusted according to the actual object (4), for example according to how delicate and heavy the object is (4).

Figure 5:
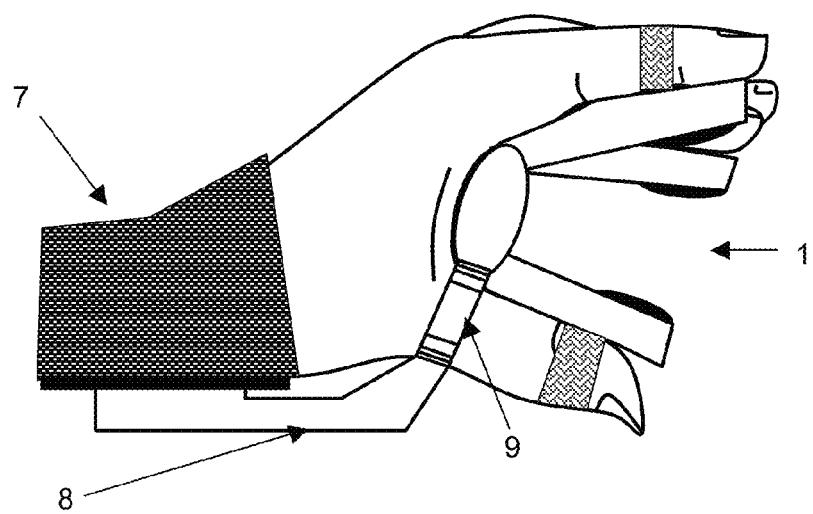
FIG. 5 is an illustration of the aid tool including mounting means.

FIG. 5 shows one embodiment of a further generalized concept of the present invention, where the aid tool (1) is coupled (8) to mounting means (7) optionally shaped as an armlet fitting tightly at a body part of the user. The coupler (8) is shown having an optional ring part (9) for the thumb to help make a stable attachment of the aid tool (1) to the hand.

The mounting means (7) may comprise fastening means to attach the mounting means (7) firmly to the body part of the user. This may be any as known in the arts such as a buckle or bask, optionally also including straps, bandage or the like to be wrapped firmly around the body part.

In an even more advanced version the mounting means (7) and/or the fastening means may be formed of a shrinkable or expandable material, such as one changing the length due to an electrical stimulus etc., for example a electrostrictive polymer, electroactive polymers or some familiar technology. Alternative the fastening means operates by pneumatics, strings, hydraulics, piezo motors, electrical and/or magnetic methods.

Figure 6A:
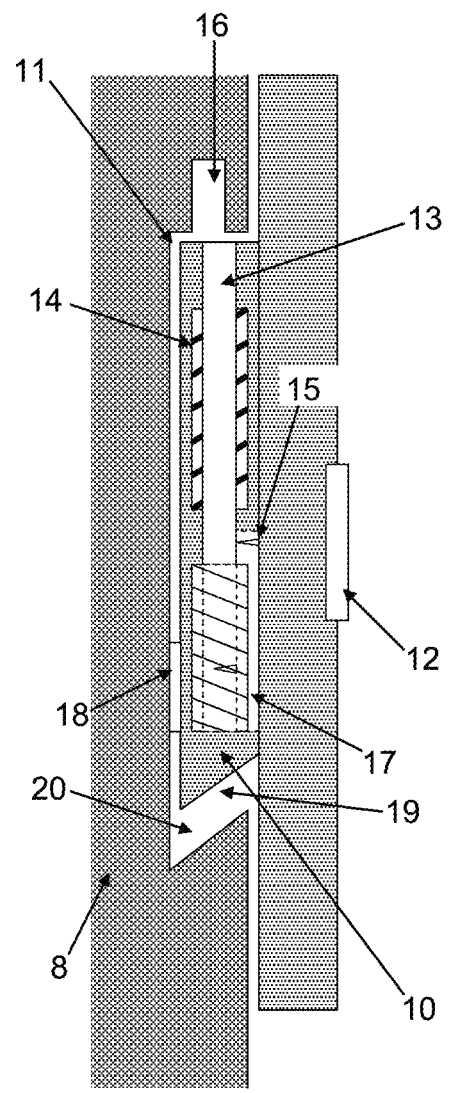
FIGS. 6A and 6B is a first embodiment of a first and second coupler adapted to attach and detach a tool to the mounting means of the present invention.
Figure 6B:
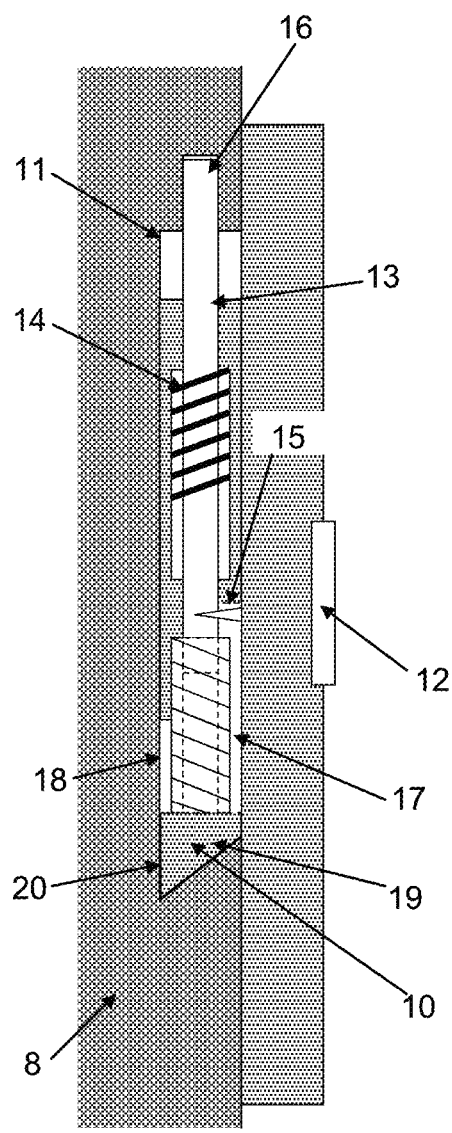

FIGS. 6A and 6B shows a embodiment of the present invention, where the mounting means (7) further comprises first coupling means (10) to be coupled to second coupling means (11) forming part of, or at least being fixed to, the coupler (8) of the tool (1), and releasing means (12) to release and detach the first (10) coupling from the second (11) coupling. The releasing means would have to be substantially easy and simple to activate due to the limited movement ability of the user.

To ensure a quick attaching and detaching of the tool (1), the coupling of the first (10) and second coupling (11) means are in one preferred embodiment based on a biased clutch system, where different biased clutches or catches may be introduced, such as a spring clutch, a diaphragm spring and/or a magnetic spring clutch etc., any as known in the arts. The term 'catch' in the following will be used in general also including clutch, pawl etc.

FIGS. 6A and 6B illustrates the basic principle where the first coupling (10) has a catch (13) being biased by biasing member (14) for example a spring, biasing the catch (13) towards a first position. A holding mechanism (15) is in a releasable manner able to hold the catch (13) in a second position, being a position where the catch (13) locks into a notch (16) of the second coupling (10). The catch (13) is forced from the first position to the second position during coupling of the first coupling (10) to the second coupling (11) by a driver (17), and the holding mechanism (15) holds the catch (13) in the second position. The driver may be activated by an activator (18) during coupling, where the activator (18) could be a switch being squeezed when the first coupler (10) is connected to the second coupler (11). The driver may be an actuator and is optionally a pneumatic, hydraulic, piezo, electroactive, electrostrictive, electrical and/or magnetic actuator.

When the holding mechanism (15) is released by activation of the release mechanism (12) the biasing member (14) forces the catch (13) to the first position, thus releasing the first (10) from the second (11) coupling.

The alternative operation would also apply to the present invention, where the biasing member (13) instead would bias the catch (13) towards the second position being the locking position when released by activating the activator (18), the driver (17) then forcing the catch (13) to the first position when the release mechanism (12) is activated. The holding mechanism (15) then would hold the catch (13) in the first position until released by the activator (18).

It is to be noted, that biasing members according to this invention in general may be any known in the art, such as like a spring, a polymer body, by pneumatic, strings, hydraulics, piezo motors, electrical, magnetic etc.

The first coupling (10) in the illustration is equipped with a shape (19) matching a second notch (20) of the second coupling (20).

The holding mechanisms (15) may be purely mechanically or electrically driven, such as by having a magnetic spring loaded catch or clutch (13) and a magnetic holding (15) mechanism being released when a circuit is short circuited or disconnected by activating the releasing means (12). Alternatively is and/or operated by pneumatics, strings, hydraulics, piezo motors etc.

FIG. 6A shows the system where the first coupling (10) is connected to the second coupling (12) and FIG. 6B shows the system when they have been coupled, where the catch (13) is pushed in a longitudinal direction into the notch (16) by a driving mechanism (17), and where this movement simultaneously pushes the shape (19) to the second notch (20), thereby firmly fixing the second coupling (10) to the second coupling (11) when the holding mechanism (15) holds the catch (13).

The aid tool (1) and/or mounting means (7) may comprise energy storing means to deliver the needed energy for example to drive the driver (17) of the biased clutch system or to operate the aid tool (1). The energy may be stored to be transferred as mechanical (for example as energy stored in a spring) or electrical energy (for example as energy stored in a battery).

The energy storing means may be an exchangeable device being prefilled with energy to be exchanged when exhausted, or may be rechargeable and being recharged during e.g. operation of the tool (1) or during coupling/decoupling of the tool (1) to and from the mounting means (7).

One main aspect of the present invention is to ensure that the mounting means is adapted to fit in a firm, stable, but also comfortable manner to the body part and at the same time form a stable platform for the tool (1) during handling. Therefore at least a part of the mounting means (7) comprises a substantially rigid shaped material being held firmly to the body part. This could be a substantially rigid sheet or body having at least one surface shaped to match the outer shape of the body part. This rigid sheet or body then comprises the first coupling (10) and is firmly held to the body part by the mounting means (7).

Figure 7A:
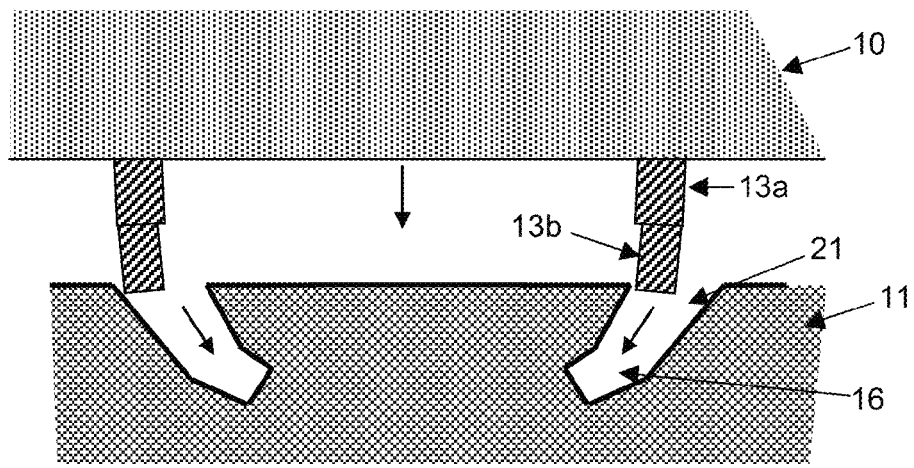
FIGS. 7A and 7B is a second embodiment of a first and second coupler adapted to attach and detach a tool to the mounting means of the present invention.
Figure 7B:
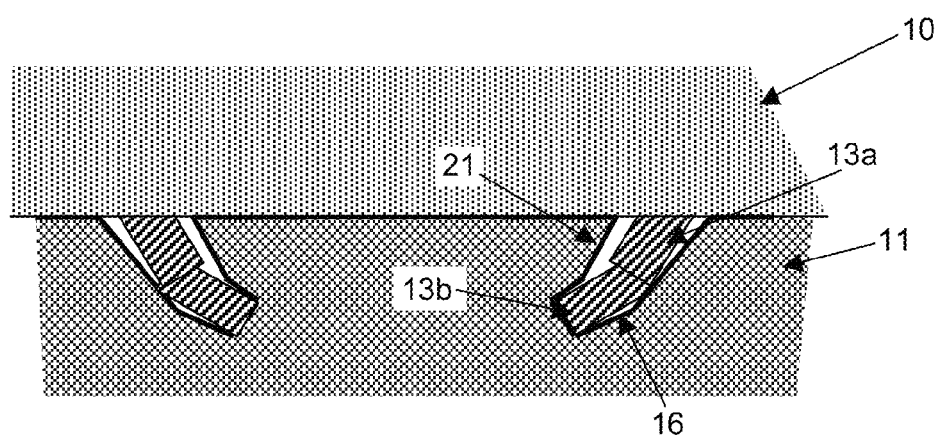

FIGS. 7A and 7B shows an alternative embodiment of a first (10) and second (11) coupler, where the catch (13) forms a rotating movement into the notch (16). The illustrated notches (16) comprises each two sections (13a, 13b) and the corresponding notches (16) of the second coupling (11) comprises inlets (21) directing the catch (13), and especially the end section (13b), into the notches (16). The first catching section (13a) is then held firmly into this position by a holding mechanism thus forming a firm coupling.

This embodiment has the advantage, that the system would need no special driving mechanism (17), the shape of the inlets (21) directing the catch (13b) into notch (16) in combination with the users themselves, would operate as driving mechanism.

FIG. 7B shows this embodiment when the two couplings (10) and (11) are coupled.

Though many of the embodiments shows couplings (10) and (11) having a planar surface, this often would not be the case, often they would be shaped in a manner practical to the surface of the body part whereto the mounting means is attached.

Figure 8:
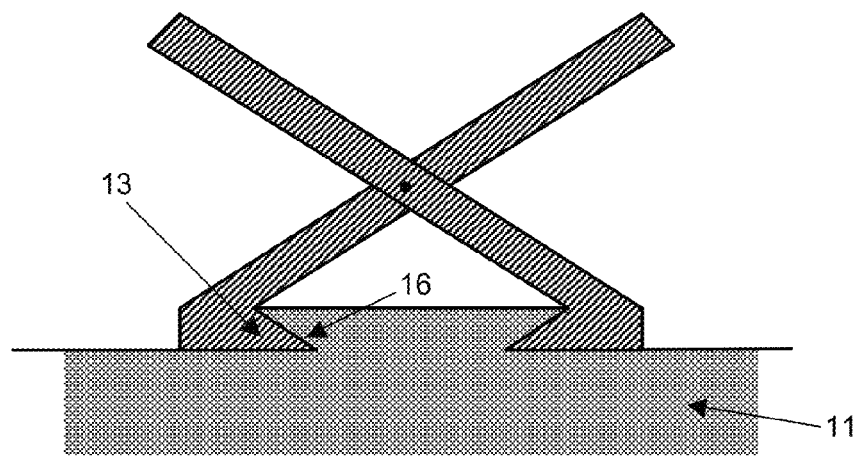
FIG. 8 is a third embodiment of a first and second coupler adapted to attach and detach a tool to the mounting means of the present invention.

FIG. 8 shows an alternative coupling where catches (13) are squeezed into notches (16), where in a related scissor like embodiment the catches (13) operates in a scissor like manner to grab into the notches (16) when squeezed by the user. Again the user operates as the driver (17).

Figure 9:
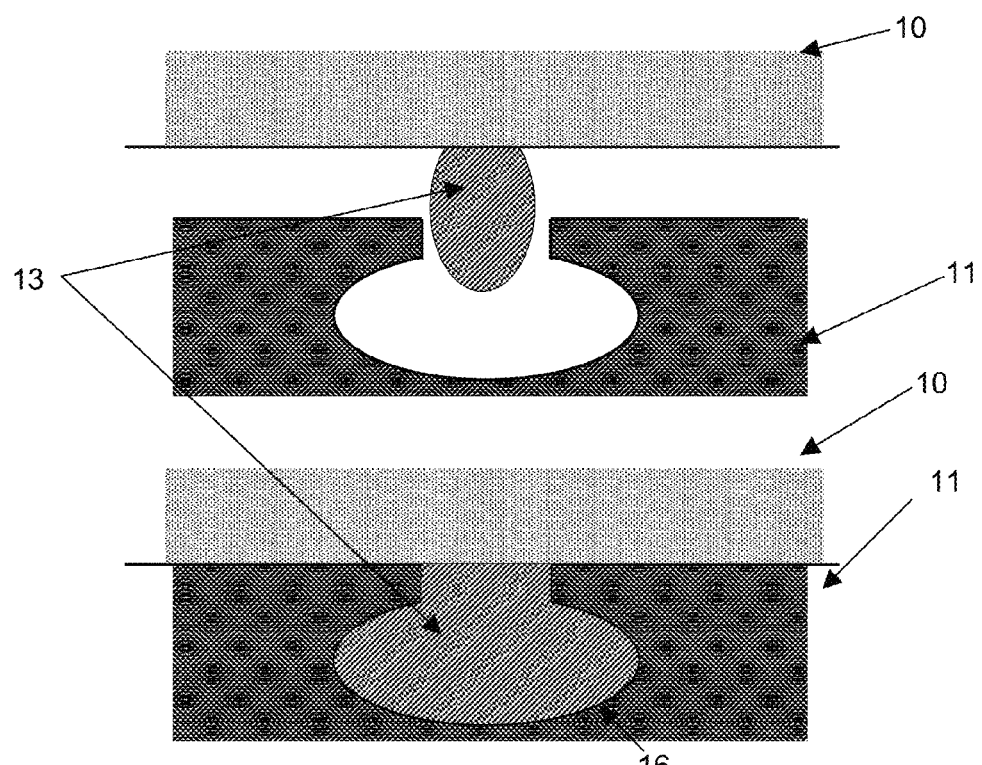
FIG. 9 is a fourth embodiment of a first and second coupler adapted to attach and detach a tool to the mounting means of the present invention.

FIG. 9 shows even an alternative coupling, where one or more catches (13) as the inflatable sections (6) is an inflatable balloon or bladder shape to be inserted into notches. When filled with a substantially incompressible media under pressure, the pressure of the media ensures the catch(es) (13) fills the notches (16) forming a stable coupling. This embodiment is especially relevant due to the system in relation to the aid tool (1) already may include means to inflate such a balloon or bladder like catch (13). The holding and release mechanism then is related to the pressure, to maintain or release the pressure and media within the catch (13). To ease coupling the catch (13) preferably would be filled at some lesser pressure during coupling.

In an alternative not illustrated embodiment, a magnetic spring clutch as for example found in air conditioning compressors is introduced with a set of coils wound in a circular fashion. The system then further comprises a flat surface having the same purpose as a flywheel. This whole unit rotates around for example the compressor driven by a belt. A driveshaft protrudes through the centre of the flat surface and attached hereto is a round disc. This disc acts like a clutch in a car. This clutch disc is in very close proximity to the flat bearing surface and held away by the use of metallic springs on the forward side of the clutch disc. When power is applied to the compressor clutch, it causes an electromagnetic field in the coils behind the clutch disc. This magnetic field attracts the clutch disc to the flat surface of the bearing like a magnet picking up a nail. The magnetic force overcomes the resistance of the springs, and the clutch locks up solid to the flat surface of the bearing and turns the compressor.

Figure 10:
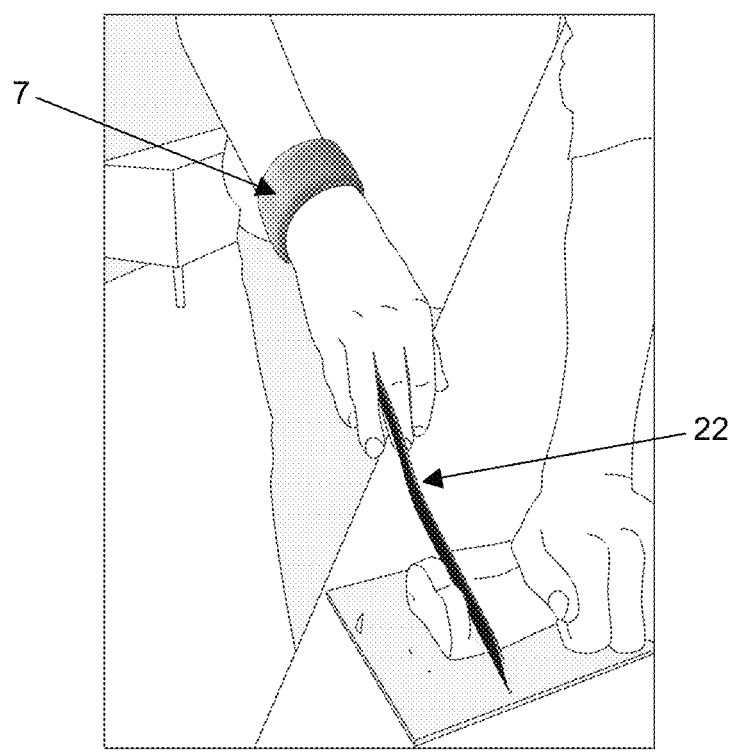
FIG. 10 shows the mounting means of the present invention being coupled to a different tool.

FIG. 10 illustrates a further important aspect of the present system utilizing the introduction of easy coupling of the tool (1) to and from mounting means (7) by first (10) and second (11) coupling elements. By equipping other tools (22) with a second coupling (11), any imaginable tool (22) may easily be attached to the mounting means (22), such as, but not limited to, a knife as illustrated. The user would therefore not need to hold the tool by the hand, but only handle the tool by using the arm and/or other body parts.

Figure 11:
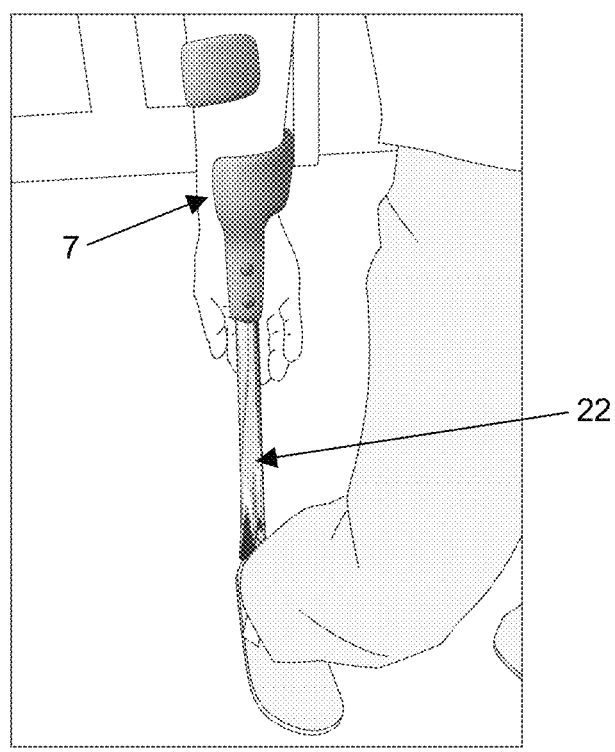
FIG. 11 is an alternative embodiment to the mounting tool according to the present invention.

FIG. 11 illustrates an embodiment of the same device where the mounting means (7) does not fully encircle the arm as such, but rather spirals on the body part. This is an embodiment especially suited for systems where the tool (1, 30) is permanently coupled to the mounting means (7), these thus being one single device to be exchanged when a new tool (1, 30) is required.

Figure 12:
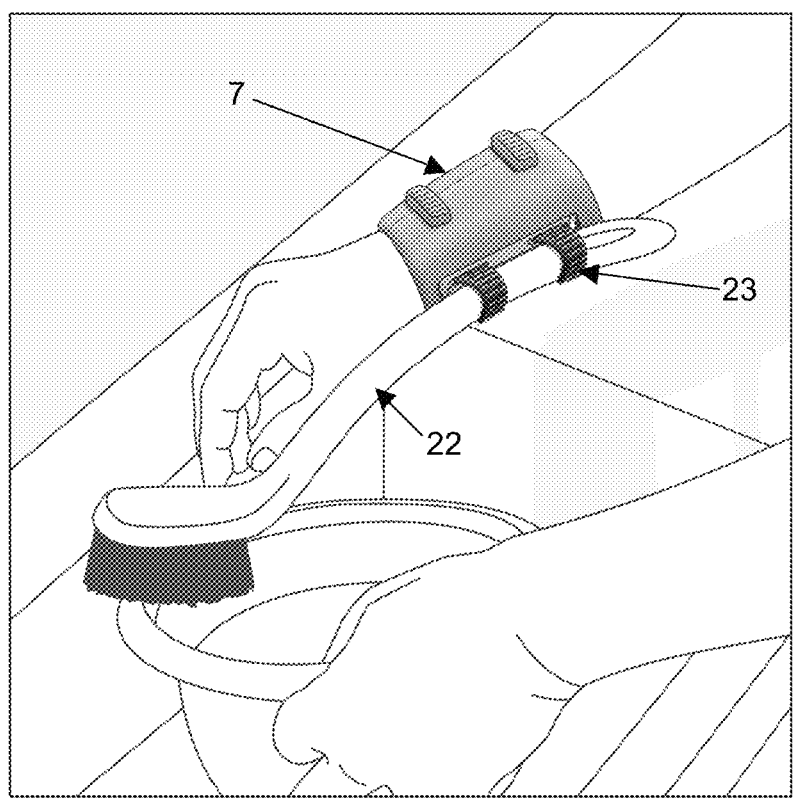
FIG. 12 is an alternative embodiment to the coupling of a tool to the mounting means according to the present invention.

FIG. 12 shows an alternative embodiment where the first coupling means (10) includes straps (23) to be tied around a part of the tool (1, 22), being the second coupling means (11) itself. The straps (23) then may be tightened in any known manner, such as by introducing buckles, the straps (23) then operating as belts, or by introducing tightening means, either a mechanical or electrical tool, to tighten the straps (23) around the tool, such as by wrapping it at a spindle in the mounting means (7), either mechanically or electrically by a small motor. The straps (23) may alternatively be some material changing the length due to an electrical stimulus etc., for example an electrostrictive polymer, electroactive polymer or some familiar technology. The tightening means then may include means to register when the tightening has reached some predetermined resistance, for example measured by a motor torque, current or voltage, numbers of turns or any other manner indicating that the tool (1, 23) is tightened enough to the mounting means (7).

It should be emphasized that any of the above coupling embodiments would naturally also be suitable for replacing the aid tool (1) with any other tool (22).

Different strategies may be introduced in relation to the mounting of the mounting means (7). Either the mounting means (7) and the tool forms one single device to be exchanged according to need, or the mounting means (7) are more or less permanently fixed to a body part, the tools (1, 22) being exchanged according to need, using first (10) and second (11) couplers.

The mounting means (7) may be such they are to be attached to the body part by the user, perhaps to be detached when not needed for example during sleep, or by for example specialists to be attached to the body part more permanently.

The mounting means (7) may be attached to the body part in a base station, for example to ensure the mounting means (7) to be fixed firmly and comfortable to the body part for secure handling of the tools. In the same manner the mounting means (7) may have to be detached in a base station. The base station may be such that it is being operated by specialists for example at a hospital, or may be at the home of the person, where the person is able to operate the base station by themselves.

For some tools (1, 22) it may of safety reason be an advantage that the tool (1, 22) automatically is released when for example applied to a certain amount of torque or force in general. This for example is well known for ski bindings, where a similar coupling mechanism in the present invention may be introduced as the first and second coupling means.

Figure 13A:
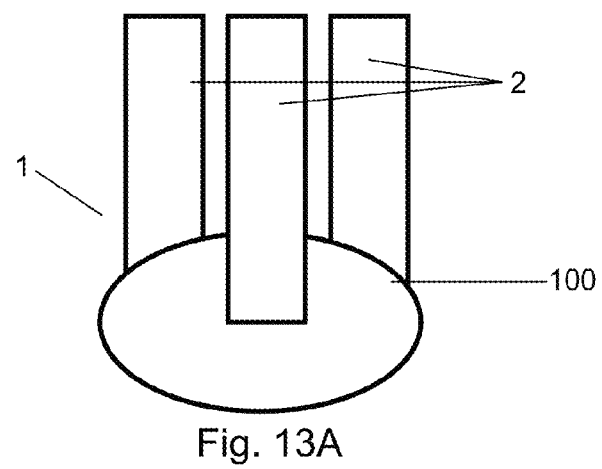
FIG. 13 is an illustration of a thumb mounted gripper and its relative degree of moveability relative to the other grippers.

FIG. 13A illustrates a preferred set up of the aid tool (1) according to the present invention where one of three grippers (2) are associated with the thumb, this being positioned parallel to the two other grippers (2) in a symmetric manner. This ensures a good and symmetric grip in many circumstances.

Figure 13B:
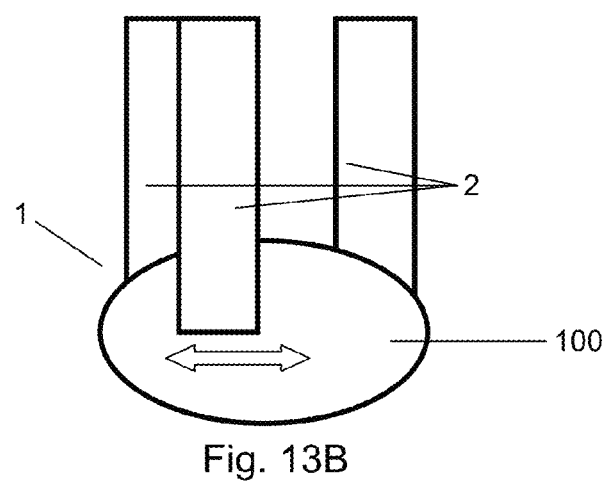
Figure 13C:
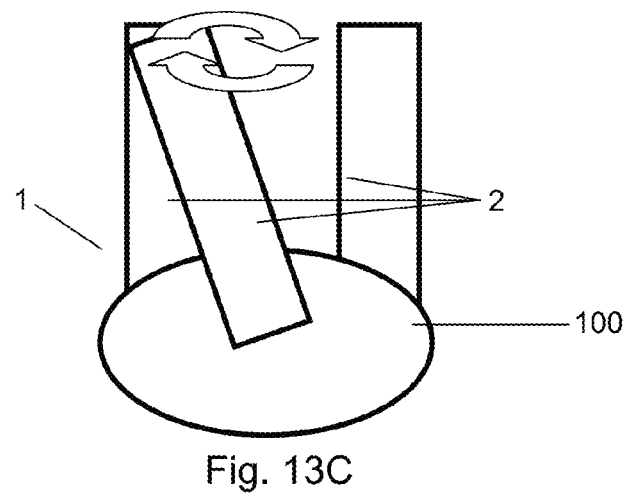

However, sometimes a grip is required/preferred involving only the thumb and one of the other fingers, usually the forefinger. Therefore in a special embodiment of the present invention, at least one of the grippers (2) (preferable but not exclusive) is able to change position, such as by a parallel shift to be positioned directly opposite to another gripper (2), as also illustrated in FIG. 13B. Alternatively or additionally, at least one of the grippers (2) is able to move with the associated finger (preferable the thumb) such that it may rotate at it fixing point to the main body (100) of the aid tool (1) at least to a degree where it can extend with at least a part of it being directly opposite to another of the grippers (2), with at least one gripper being positioned with an angle different from 0 degrees relative to this opposite gripper (2), as also illustrated in FIG. 13C.

When e.g. activation switch (5) is activated the grippers (2) will lock uni-directionally into these positions such as it has been described previously.

The mounting means (7) may be equipped with inflatable bags internally in a manner, where, when the bags are filled with some media at some pressure, then the bags squeezes to the body part whereto the mounting means (7) are to be fixed. The more media filled into the bags, the more tightly the mounting means (7) will be fixed to the body part.

Figure 14:
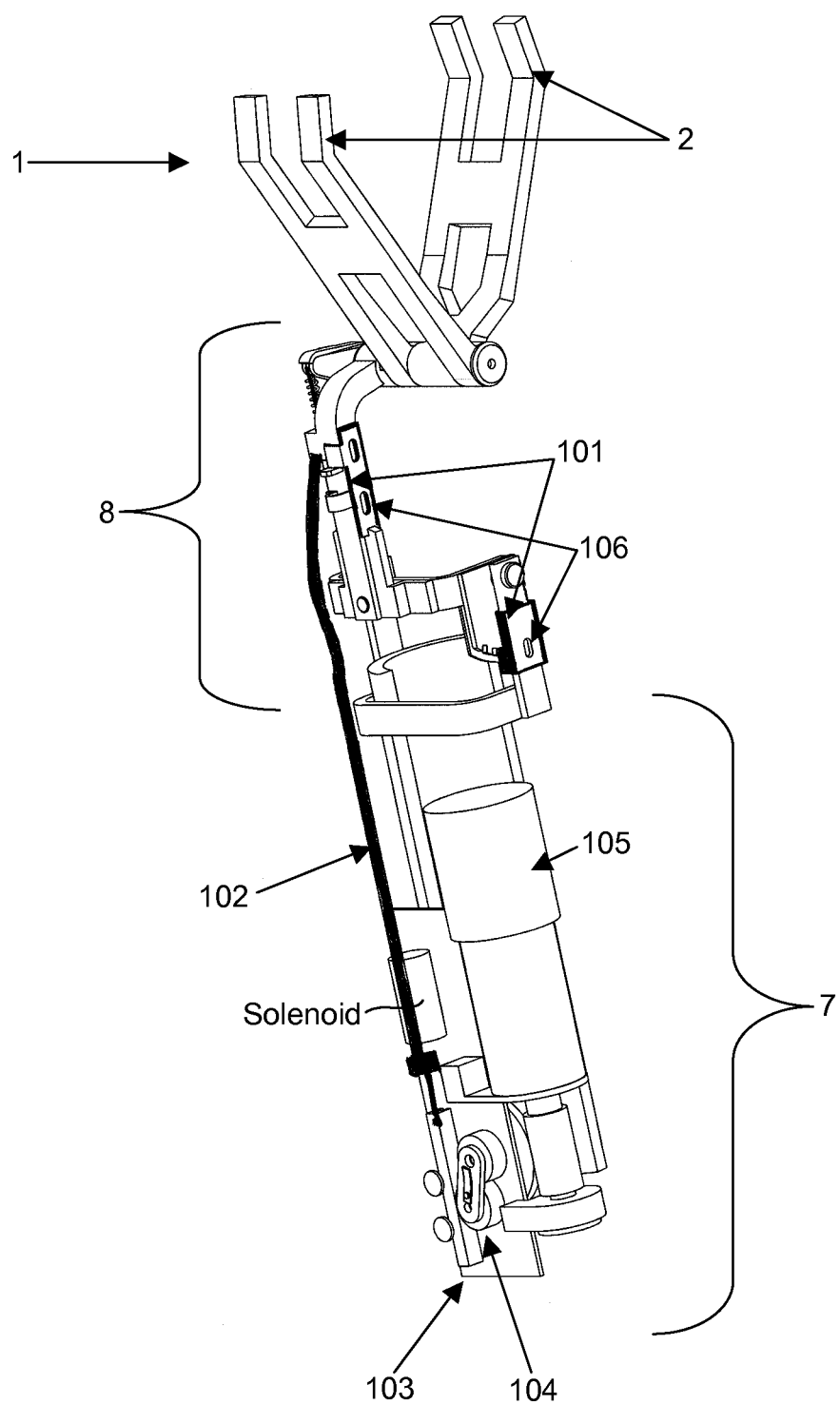
FIG. 14 is an illustration of one embodiment of the aid tool with mounting means and flexible joints.

FIG. 14 illustrates one non-limiting embodiment of the aid tool (1) according to the present invention.

The figure shows the aid tool (1) with the grippers (2) being coupled (8) to the mounting means (7), and where the coupling (8) comprises two flexible joints (101) where they respectively gives an up-and-down and a side-to-side movement, or rotation, of the aid tool (1) in relation to the mounting means (7). These flexible joints (101) however are adapted to lock in their rotation when the aid tool (1) is activated, thus 'freezing' the relative positions at least substantially into their relative positions at the time of activation.

At least one of the grippers (2) is driven by the wire (102) pulling the grippers (2), and where the wire (102) is connected to a rack (103), where the rack (103) again is being operated by a pinion-system (104) in a manner where the teeth of the rack and connected pinion is shaped such that the connected pinion may prevent the rack from movement in the direction to loosen the grip of the grippers (2) when the system as activated, but does not prevent it to move in the direction to fasten the grip (this being another example of the principle of unidirectional tightening explained earlier).

A craftsman will recognize how to make the teeth of rack (103) and pinion (104) to achieve this, or any other manner where a similar effect may be achieved for example by having the pinion (104) locking in rotation in one but not the opposite direction, by motor control, by actuator control etc. Further the illustrated embodiment comprises an electric motor (105) to drive e.g. the pinion system (104). The present invention is not limited to the exact manner this is achieved, but to the important aspect, that even though the grippers (2) have been locked by activation of the system, this is only to be understood as locking in the loosening direction, not in the tightening direction of the grippers (2). The persons using the aid tools (1) may themselves fasten the grip by tightening the grippers (2) with their own fingers, the system preventing the grip to be loosened again even though the person loosen the grip of the fingers, at least until the system is deactivated again.

In one preferred embodiment the system operates such that after activation the grip of the grippers (2) will be tightened slightly more than it was at the time of activation, in order to tighten the grip slightly more. How much the grippers (2) further will tighten the grip may depend on several factors, like being pre-defined, depending on some activation of the user of the aid tool (2) optionally operated by the second hand and/or depending on a strain gauge of one or more of the grippers (2) adapted to measure the tightening force, where e.g. one or more of these may be used by and algorithm to calculate the further tightening grip.

Figure 15:
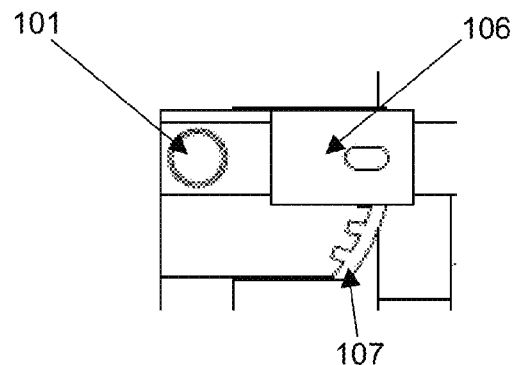
FIG. 15 is an illustration of one embodiment of the locking mechanism of the flexible joints.

In one embodiment the locking mechanism of the flexible joints (101) is also driven by wires as (102) and may in one embodiment comprise a latch (106) driven by the wires, where the latch comprises a number of 'freezing' positions according to the actual position of the aid tool (1) to the mounting means (7) when activated. This may constitute a pin being pushed into the nearest of a number of teeth of a rack-like structure (107) as illustrated in FIG. 15, where the rack-like structure (107) are attached to one 'side' of the joint (101) and the pin to the other 'side', thus when activated the pin locks into the nearest position of the rack like structure at activation, thus freezing it into this position. Though this is the illustrated embodiment any other systems as they will be well known to a craftsman will also apply to the present invention.

Figure 16:
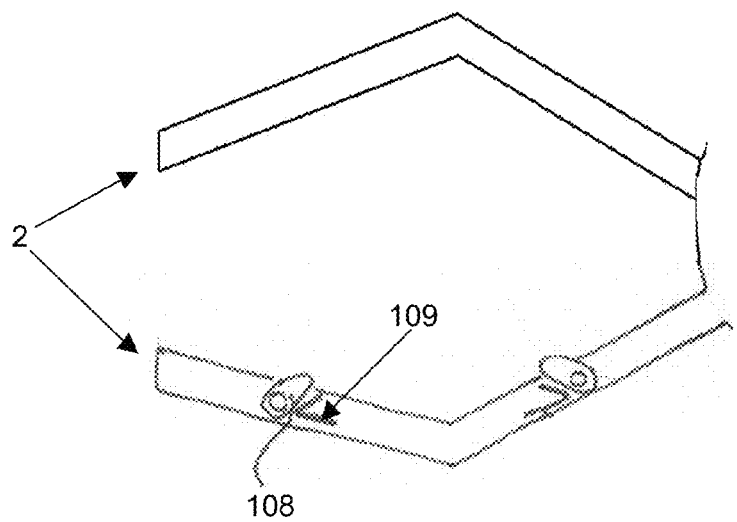
FIG. 16 is an illustration of grippers with rotation contact sections.

FIG. 16 illustrates a further embodiment that might be incorporated into the system. In many cases the hand needs to hold onto an object to be involved in a rotating, often a screwing, movement, such as when screwing the lid on and off a glass of jam. To get a firm grip onto such objects often requires an even more firm grip than when just holding onto an object. Therefore the grippers (2) may comprise rotation contact sections (108) being squeezed to press on the object (4) with a force depending on the rotation, such as the illustrated example, where the rotation contact sections (108) by friction in the contact to a object (4), are moved against a spring element (109) adapted to squeeze the rotation contact sections (108) against the object (4). Such systems are well established e.g. for oil filters, and any embodiment as it will be known by a craftsman will apply to the present invention.

In summary, the operation of the aid tool (1) according to the main embodiment is:
1. The person using the aid tool (1) positions it to form a loose grab on an object (4)
2. When the aid tool (1) is in position an activation switch (5) is activated
3. The locking of the grippers (2) and the flexible joints (101), the grippers (2) being locked unidirectional.
4. A hold of the object (4) is established.

Although the invention above has been described in connection with a preferred embodiment of the invention, it will be evident for a person skilled in the art that several modifications are conceivable without departing from the invention as defined by the following claims.

What is claimed is:

1. An aid tool comprising at least two grippers where the grippers are adapted to move at least in directions to grab and release an object, wherein an activation of the aid tool locks the grippers unidirectionally such that the grippers are locked from movement in the direction to release the object;
wherein a coupling couples the grippers to mounting means, and where the coupling comprises two flexible joints, one flexible joint giving an up-and-down rotation and the other flexible joint giving a side-to-side rotation of the grippers in relation to the mounting means;
wherein each gripper further comprises means to attach each gripper to a finger of a person; and
wherein an activation switch is positioned on a gripper of the at least two grippers and is adapted to be activated by a finger to which the gripper is adapted to be attached.

2. The aid tool according to claim 1, wherein said aid tool further comprises means to establish a hold of the object,
wherein the hold is established, after grabbing the object and after activation to lock the grippers unidirectionally, the hold being established by the grippers moving further in the direction to grab the object to form a slightly tighter grab than the grab formed at the time of activation.

3. The aid tool according to claim 2, wherein the grippers further comprise elastically deformable contact sections.

4. The aid tool according to claim 1, wherein the aid tool is activated by pressing the activation switch with a predetermined force.

5. The aid tool according to claim 1, wherein the grippers are adapted to be positioned between the fingers of the person and the object when grapping the object.

6. The aid tool according to claim 1, wherein the flexible joints are adapted to lock in their movement or rotation when the aid tool is activated, thus fixing relative positions of the flexible joints into their relative positions at the time of activation.

7. The aid tool according to claim 1, wherein the aid tool comprises means for storing energy.

8. The aid tool according to claim 1, wherein:
the aid tool is adapted to be operated by the person to grab the object, wherein the aid tool is positioned to form a loose grab on the object,
so that when the aid tool is in position the activation switch is activated,
the activation further activates the locking of the flexible joints and locks the grippers unidirectionally, and
finally the activation activates a hold of the object to be established.

* * * * *